(12) United States Patent
Kowarschik et al.

(10) Patent No.: US 11,707,240 B2
(45) Date of Patent: Jul. 25, 2023

(54) VISUALIZATION METHOD AND APPARATUS

(71) Applicant: Siemens Healthcare GmbH, Erlangen (DE)

(72) Inventors: Markus Kowarschik, Nuremberg (DE); Sebastian Schafer, Madison, WI (US)

(73) Assignee: Siemens Healthcare GmbH, Erlangen (DE)

( * ) Notice: Subject to any disclaimer, the term of this patent is extended or adjusted under 35 U.S.C. 154(b) by 262 days.

(21) Appl. No.: 17/152,078

(22) Filed: Jan. 19, 2021

(65) Prior Publication Data

US 2021/0228169 A1    Jul. 29, 2021

(30) Foreign Application Priority Data

Jan. 28, 2020   (DE) .................... 10 2020 200 967.8

(51) Int. Cl.
*A61B 6/00*      (2006.01)
*G06T 5/50*      (2006.01)
*G06T 7/00*      (2017.01)

(52) U.S. Cl.
CPC .............. *A61B 6/486* (2013.01); *A61B 6/481* (2013.01); *G06T 5/50* (2013.01); *G06T 7/0012* (2013.01); *G06T 2207/10072* (2013.01); *G06T 2207/30104* (2013.01)

(58) Field of Classification Search
None
See application file for complete search history.

(56) References Cited

U.S. PATENT DOCUMENTS

| | | | |
|---|---|---|---|
| 10,134,144 B2 * | 11/2018 | Mistretta | G06T 7/246 |
| 2004/0142485 A1 * | 7/2004 | Flower | A61B 3/0058 |
| | | | 436/172 |
| 2010/0014735 A1 * | 1/2010 | Bi | G01R 33/5635 |
| | | | 382/131 |
| 2014/0094680 A1 * | 4/2014 | Kowarschik | A61B 6/4464 |
| | | | 600/407 |

OTHER PUBLICATIONS

Davis, Brian, et al. "4D digital subtraction angiography: implementation and demonstration of feasibility." American Journal of Neuroradiology 34.10 (2013): 1-8.

* cited by examiner

*Primary Examiner* — Vu Le
*Assistant Examiner* — Courtney Joan Nelson
(74) *Attorney, Agent, or Firm* — Lempia Summerfield Katz LLC

(57) ABSTRACT

An inverse visualization of a time-resolved angiographic image data set of a vascular system of a patient that was recorded by a medical imager during the flow of a contrast medium through the vascular system is provided. The time-resolved angiographic image data set of the vascular system has a temporal sequence of frames of the vascular system corresponding to the contrast medium filling process. A data set from bolus arrival times for each pixel or voxel is determined. The bolus arrival time corresponds to the time in the temporal sequence at which a predetermined contrast enhancement due to the contrast medium filling first occurs. A data set of temporally inverted bolus arrival times with respect to the contrast medium filling is determined for each pixel or voxel, resulting in a temporally inverted sequence of frames with respect to the contrast medium filling. The time-resolved angiographic image data set in the temporally inverted sequence is visualized.

14 Claims, 2 Drawing Sheets

VISUALIZATION METHOD AND APPARATUS

RELATED CASE

This application claims the benefit of German Application 10 2020 200 967.8, filed on Jan. 28, 2020, which is hereby incorporated by reference in its entirety.

FIELD

The present embodiments relate to a method for creating an inverse visualization of a time-resolved angiographic image data set of a vascular system.

BACKGROUND

Diagnosis and treatment of clinical conditions requires a particularly good and precise depiction of vascular systems in organs. This is and remains a challenge especially in particularly complex structures such as the brain. A number of methods for depicting vascular systems within organs are known, for example CT angiography, MR angiography, or digital subtraction angiography.

In the simplest two-dimensional variant of digital subtraction angiography (DSA), an X-ray angiography system (for example by means of a C-arm system) creates two-dimensional projection images of a patient's vascular system to be examined before and during the introduction of a contrast medium. This results in a projection image without contrast medium, also called a mask image, and further projection images with contrast medium distribution in the vascular system, so-called fill projection images. The digital mask image is subtracted from the subsequent fill projection images. The only parts that remain are those that differ, i.e., generally precisely the vascular system.

Three-dimensional digital subtraction angiography (3D DSA) enables high-resolution depiction of, for example, contrasted vascular systems as 3D volumes. For this purpose, typically a mask run is performed without contrast medium and one or more fill runs are performed with a contrast medium flow and herein a series of projection images created in each case. Here, the two-dimensional projection images usually originate from a recording protocol for a C-arm X-ray device (e.g., a cone beam CT) rotating about the patient. This is then followed either by first subtracting the series and then reconstructing the remaining series to produce a volume or first reconstructing the series to produce volumes and then subtracting the volumes.

For four-dimensional DSA, a three-dimensional data set with preferably stationary contrast medium filling is processed with a series of two-dimensional projection images that were recorded during a contrast medium delivery and/or clearance phase to produce a time-resolved series of three-dimensional DSA image data. Here, the standardized two-dimensional projection images are back-projected together with temporal information into volume elements of the 3D data set. The result is 3D volumes of the vascular system with additional temporal information on the blood flow since the contrast medium flow is usually recorded with 30 images per second, for example. Alternatively, a 4D DSA data set can be generated from 3D DSA, wherein a series of two-dimensional projection images is recorded during the delivery and the clearance phase of the contrast medium. First, static 3D DSA is generated from this projection data. Then, the 3D volume and the 2D projection image are compared for each projection, and the fill status of the 3D volume is adjusted. Typical 4D DSA is described in the article by Davis et al., 4D Digital Subtraction Angiography: Implementation and Demonstration of Feasibility, American Journal of Neuroradiology, Vol. 34, issue 10, 2013.

Four-dimensional DSA is then visualized as a scene in which the flow of contrast medium is shown in the correct temporal sequence. However, here, vascular overlap and foreshortening can also have the result that vessels that are filled with contrast medium at a later time are only inadequately recognizable.

SUMMARY AND DETAILED DESCRIPTION

The object is to provide a method that also enables particularly good recognizability of vessels of the vascular system that are filled with contrast medium at a later time. It is also an object to provide a suitable apparatus for carrying out the method.

A method is provided for creating an inverse visualization of a time-resolved angiographic image data set of a vascular system. An apparatus is also provided. Advantageous embodiments are discussed below.

The method according to one embodiment for creating an inverse visualization of a time-resolved angiographic image data set of a vascular system of a patient that was recorded by a medical imaging facility or imager during the flow of a contrast medium (and/or marked blood components) through the vascular system includes multiple acts. The time-resolved angiographic image data set of the vascular system, which has a temporal sequence of frames of the vascular system at N times (t(1) . . . t(N)) corresponding to the contrast medium filling process, is provided. A data set from bolus arrival times $t_{BAT}$ for each pixel or voxel of the frames of the recorded vascular system is determined. The bolus arrival time corresponds to the time (t(i)) in the temporal sequence at which a predetermined contrast enhancement due to the contrast medium filling first occurs. A data set of temporally inverted second bolus arrival times $t_{BAT}^{in}(v)$ with respect to the contrast medium filling for each pixel or voxel of the recorded vascular system, in particular using the formula $t_{BAT}^{in} = t(N) - t_{BAT}$, and from this a temporally inverted sequence of frames with respect to the contrast medium filling, are determined. At least a part of the time-resolved angiographic image data set of the vascular system in the temporally inverted sequence with respect to the contrast medium filling is visualized.

The method according to one embodiment ascertains a temporally inverted visualization of the contrast medium filling process within the vascular system and is able to display this visualization. This visualization is not simply a filling played backwards—it also corresponds to a hypothetical filling of the vascular system with a completely reversed contrast medium direction of flow. As a result, in addition to the venous vessels, this also in particular enables optimal depiction of the vessels that are masked by vascular overlap and foreshortening with the correct direction of flow. The method enables the recognizability of malformations and disorders of the vascular system that require treatment to be greatly improved when depicting vascular systems, for example in the brain. This enables the attending physician to achieve improved diagnosis and this in turn results in improved therapeutic results.

In this context, a frame is not necessarily a complete 2D projection or a 3D volume image, but optionally can also be understood to be a 2D or 3D "constraining image" that is common with DSA, which only maps a subregion, i.e., for example, the vascular system without surrounding tissue (i.e. only the pixels or voxels of the vascular system). Generally, a unique time is assigned to each frame. In practice, the temporal sequence can correspond to consecutive numbering (for example 1, 2 ... N) or actual consecutive time units $$\left(\frac{1}{30}s, \frac{2}{30}s \ldots \frac{N}{30}s\right).$$

A common DSA frame rate can, for example, be several or a large number of (for example 30) frames per second.

For each pixel or voxel of the vascular system depicted, the bolus arrival times correspond to the time in the temporal sequence of the frames at which a predetermined contrast enhancement due to the contrast medium filling first occurs. The prior art contains a large number of different definitions and determination methods for the bolus arrival times; the method is, however, independent of the respective definition or determination method.

According to one embodiment, the time-resolved angiographic image data set of the vascular system is formed by a four-dimensional subtraction angiography data set that has a temporal sequence of volume frames (e.g., constraining volumes) of the vascular system corresponding to the contrast medium filling process. There are a large number of different recording protocols and/or injection protocols and a large number of reconstruction algorithms and possibilities for recording such time-resolved three-dimensional subtraction angiography data sets. The method is independent of the method with which the four-dimensional subtraction angiography data set was compiled.

4D DSA can, for example, be created as described in the introduction. A three-dimensional data set with preferably stationary contrast medium filling is processed with a series of two-dimensional projection images that were recorded during a contrast medium delivery and/or clearance phase to produce a time-resolved series of three-dimensional DSA image data. The 2D projection images are back-projected together with temporal information into volume elements of the 3D data set. The result is a series of 3D volumes of the vascular system with additional temporal information on the blood flow.

According to a further embodiment, the time-resolved angiographic image data set of the vascular system is formed by a series of two-dimensional subtraction angiography images. Here, generally projection images are used that were recorded in a time-resolved manner by an X-ray device, for example a C-arm X-ray device.

According to a further embodiment, the time-resolved angiographic image data set of the vascular system is formed by a four-dimensional computed tomography data set or a four-dimensional magnetic resonance data set. Methods for recording angiography data sets are known in both computed tomography and magnetic resonance tomography and can be used for the method.

According to a further embodiment, the predetermined contrast enhancement due to the contrast medium filling is at least 10% of the maximum contrast. Therefore, this means that, for each pixel or voxel, this time corresponds to the bolus arrival time at which the contrast enhancement due to the contrast medium filling is 10% or more for the first time. This corresponds to a common and technically feasible definition of the bolus arrival time. Alternatively, it is also possible, for example, for 20% or 25% to be used.

According to a further embodiment, the time-resolved angiographic image data set of the vascular system is displayed or played back as a scene on a display unit (display or display screen) in the temporally inverted sequence with respect to the contrast medium filling. A physician can use a one-off or continuously repeating scene to recognize vascular processes that would be hidden with the normal direction of filling and thus provide a better diagnosis.

For a comprehensively recognizable and diagnosable image of the vascular process, the time-resolved angiographic image data set of the vascular system is particularly advantageously displayed or played back on a display unit as a scene in the temporal sequence corresponding to the process with respect to the contrast medium filling and the temporally inverted sequence in alternation.

According to a further embodiment, the visualization has a color gradient. Thus, for example, pixels or voxels with the same seniority can be depicted in the same colors.

According to a further embodiment, at least one pre-trained machine learning algorithm is used to carry out the method. This can, for example, divide the vessels into arterial and venous structures in order to enable the observer to analyze a further depth level. The algorithm is pretrained using heuristic information such as the position of the vessel in the tree (distance to the catheter), previous vascular ramifications, contrast medium pulsation strength etc.

Another embodiment is an apparatus for carrying out the method. An image processing unit (image processor) for processing image data sets, a computing unit (computer) for carrying out computing operations, i.e. the determination of the bolus arrival times and the inverse bolus arrival times, a storage unit (memory) for storing data sets, i.e., for example, the time-resolved angiographic image data set of the vascular system, a system controller (controller) for actuating the apparatus and a display unit for displaying image data. The apparatus advantageously also has a medical imaging facility (imager or scanner) for recording image data sets. This can, for example, be a C-arm X-ray device embodied for rotation angiography.

BRIEF DESCRIPTION OF THE DRAWINGS

Further advantageous embodiments are explained in more detail in the following with reference to schematically depicted exemplary embodiments in the drawing without restricting the invention to these exemplary embodiments. The figures show.

DETAILED DESCRIPTION OF THE PREFERRED EMBODIMENTS

Figure 1:
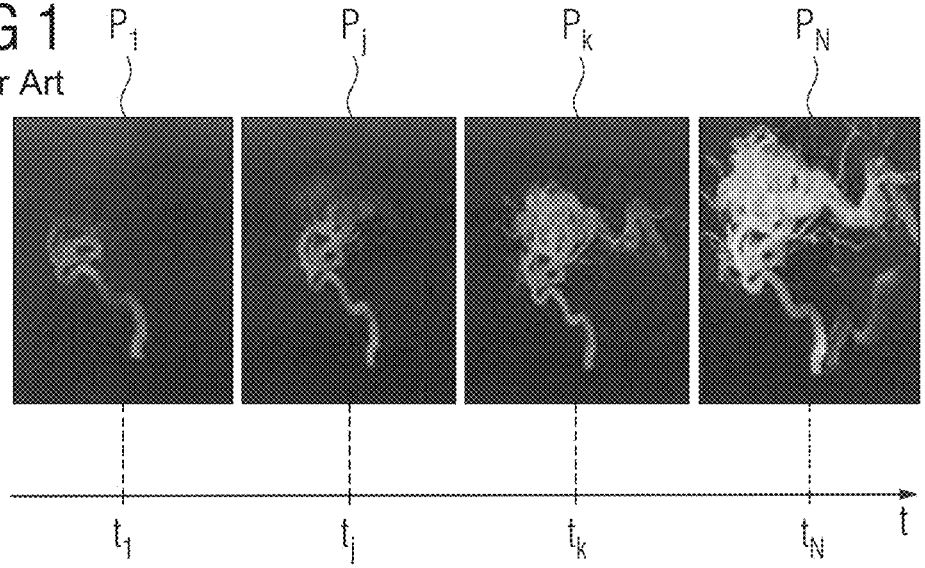
FIG. 1 shows a series of four time-resolved frames of a vascular system through which a contrast medium flows according to the prior art.

FIG. 1 shows a section from a four-dimensional subtraction angiography data set according to the prior art with a temporal sequence of volume frames (e.g., constraining volumes) of a vascular system corresponding to the contrast medium filling process. By way of example, this shows four volume frames along a time axis t, wherein the first volume frame $P_1$, the (last) N-th volume frame $P_N$ with complete filling and two volume frames located therebetween temporally, the j-th volume frame $P_j$ and the k-th volume frame $P_k$, are shown. It is also possible in each case for there to be a large number of volume frames between the volume frames shown, but these are not shown here. The totality of the volume frames forms a time-resolved series. The four-dimensional subtraction angiography data set can be recorded and determined as described above or in another manner. Thus, typically, a mask run can be performed without contrast medium and one or more fill runs performed with a contrast medium flow and a series of projection images created in each case. Here, the two-dimensional projection images usually originate from a recording protocol for a C-arm X-ray device (e.g., a cone beam CT) rotating about the patient. This is then followed either by first subtracting the series and then reconstructing the remaining series to produce a volume or first reconstructing the series to produce volumes and then subtracting the volumes. The vascular system can, for example, be a vascular tree in the brain (e.g., with a cerebral arteriovenous malformation), the heart or another organ.

In the prior art, such a four-dimensional subtraction angiography data set is displayed or played back as a scene in the temporal sequence corresponding to the process with respect to the contrast medium filling. This enables visualization of blood vessels that are otherwise unrecognizable. However, here, vascular overlap and foreshortening give rise to the problem that vessels that are filled with contrast medium at a later time (for example venous vessels) can only be recognized inadequately. Recognizability can be further improved using the method according to embodiments described in the following with which visualization of an inverse filling of the vessels from the known time-resolved angiographic image data set, for example the four-dimensional subtraction angiography data set, is calculated algorithmically.

Figure 2:
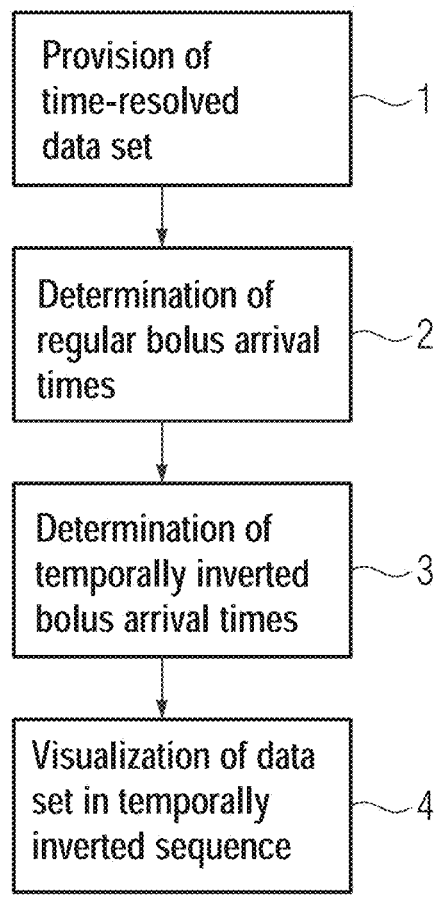
FIG. 2 shows a sequence of acts of the method according to one embodiment.

FIG. 2 shows the course of a method according to one embodiment. In a first act 1, a time-resolved angiographic image data set of the vascular system is provided. This data set maps a temporal sequence of frames of the vascular system at N times (t(1), . . . , t(N)) corresponding to the actual contrast medium filling process. The time-resolved angiographic image data set can, for example, be a four-dimensional subtraction angiography data set (time-resolved volume data set) or a time-resolved two-dimensional subtraction angiography data set. It is also possible for four-dimensional computed tomography data sets or magnetic resonance data sets to be used. The data sets were recorded during the passage of a contrast medium through the vascular system. In this context, a frame is not necessarily a complete 2D projection or a 3D volume image, but optionally can also be understood to be a common DSA 2D or 3D "constraining image," which only maps a subregion, i.e. for example the vascular system without surrounding tissue (i.e. only the pixels or voxels of the vascular system). Generally, a unique time is assigned to each frame. In practice, the temporal sequence can correspond to consecutive numbering (for example 1, 2 . . . N) or actual consecutive time units $$\left(\frac{1}{30}s, \frac{2}{30}s \ldots \frac{N}{30}s\right).$$

A common DSA frame rate can, for example, be 30 (25, 35 . . . ) frames per second. The provision can, for example, be performed such that the data set is provided from a storage unit or transferred from an external database.

It is also possible for a corresponding data set to be recorded and preprocessed (for example reconstructed) by a medical imaging facility in a preliminary step.

In a second act 2, a data set is determined from bolus arrival times $t_{BAT}$ for each pixel or voxel of the frames of the recorded vascular system. Herein, the bolus arrival time corresponds to the time (t(i)) (wherein i=1 . . . N) in the temporal sequence at which a predetermined contrast enhancement due to the contrast medium filling first occurs. There are different possibilities for the definition and determination of the bolus arrival times. For example, the predetermined contrast enhancement due to the contrast medium filling can be at least 10% of the maximum contrast in order to count as a bolus arrival time. Therefore, this means that, for each pixel or voxel, this time corresponds to the bolus arrival time at which the contrast enhancement due to the contrast medium filling is 10% or more for the first time. This corresponds to a common and technically feasible definition of the bolus arrival time. Alternatively, it is also possible, for example, for 20% or 25% to be used. The bolus arrival times are, for example, ascertained or calculated by an image processing unit and/or a computing unit.

In a third act 3, a data set of temporally inverted second bolus arrival times $t_{BAT}^{in}$ with respect to the contrast medium filling is then determined for each pixel or voxel of the recorded vascular system. The formula $t_{BAT}^{in}=t(N)-t_{BAT}$ is used for this purpose. For example, when N=304 (i.e. the last time is t(304)=304) and a specific voxel was first filled at the time $t_{BAT}(72)=t(72)=72$, the following is obtained: $t_{BAT}^{in}(72)=t(304)-t_{BAT}(72)=304-72=232$. Then a temporally inverted sequence of frames with respect to the contrast medium filling is determined from the data set of temporally inverted second bolus arrival times $t_{BAT}^{in}$ with respect to the contrast medium filling for each pixel or voxel. Here, it is again possible, for example, to use a computing unit to calculate the inverted bolus arrival times.

In a fourth act 4, the time-resolved angiographic image data set of the vascular system in the temporally inverted sequence with respect to the contrast medium filling is visualized, i.e., for example displayed as an inverted scene on a display unit. This visualization is not simply a filling played backwards—it also corresponds to a hypothetical filling of the vascular system with a completely reversed direction of flow of the contrast medium. As a result, in addition to the venous vessels, this also in particular enables optimum depiction of the vessels that are masked by vascular overlap and foreshortening with the correct direction of flow.

For particularly good recognizability of the vascular system, it is, for example, possible for the time-resolved angiographic image data set of the vascular system to be displayed or played back as a scene on a display unit in the temporal sequence corresponding to the process with respect to the contrast medium filling and the temporally inverted sequence in alternation.

It is also possible within the scope of the method according to some embodiments to use an algorithm for machine learning, for example, to determine data such as the bolus arrival times or the inverse bolus arrival times.

Figure 3:
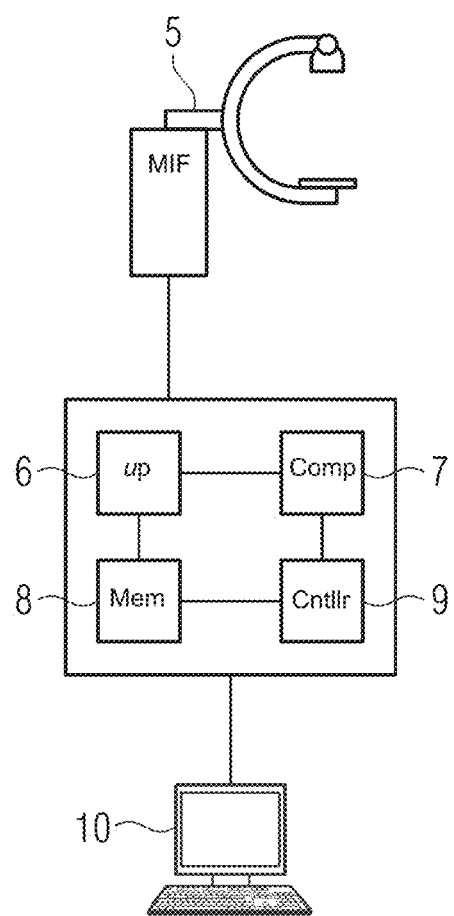
FIG. 3 shows an apparatus for carrying out the method according to one embodiment.

FIG. 3 shows an apparatus for carrying out the method according to one embodiment. This has a medical imaging facility 5 for recording image data sets, an image processing unit 6 for processing image data sets, a computing unit 7 for carrying out computing operations, a storage unit 8 for storing data sets, a system controller 9 for actuating the entire apparatus and a display unit 10 for displaying image data. The medical imaging facility 5 can, for example, be formed by a C-arm X-ray device embodied for rotation angiography.

Some embodiments may be briefly summarized as follows: for improved visualization of, for example, masked vascular processes, a method for creating an inverse visualization of a time-resolved angiographic image data set of a vascular system of a patient that was recorded by a medical imaging facility during the flow of a contrast medium (and/or marked blood components) through the vascular system with the following acts is performed: provision of the time-resolved angiographic image data set of the vascular system that has a temporal sequence of frames of the vascular system at N times (t(1), . . . , t(N)) corresponding to the contrast medium filling process, determination of a data set from bolus arrival times $t_{BAT}$ for each pixel or voxel of the frames of the recorded vascular system, wherein the bolus arrival time corresponds to the time (t(i)) in the temporal sequence at which a predetermined contrast enhancement due to the contrast medium filling first occurs, determination of a data set of temporally inverted second bolus arrival times $t_{BAT}^{in}$ with respect to the contrast medium filling for each pixel or voxel of the recorded vascular system, in particular using the formula $t_{BAT}^{in}=t(N)-t_{BAT}$, and from this a temporally inverted sequence of frames with respect to the contrast medium filling, and visualization (of at least a part) of the time-resolved angiographic image data set of the vascular system in the temporally inverted sequence with respect to the contrast medium filling.

It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A method for creating an inverse visualization of a time-resolved angiographic image data set of a vascular system of a patient that was recorded by a medical imaging facility during a flow of a contrast medium and/or marked blood components through the vascular system, the method comprising:

accessing the time-resolved angiographic image data set of the vascular system, the time-resolved angiographic image data set having a temporal sequence of frames of the vascular system at N times (t(1), . . . , t(N)) corresponding to the contrast medium and/or marked blood components filling process, determining a data set from bolus arrival times $t_{BAT}$ for each pixel or voxel of the frames of the recorded vascular system, wherein the bolus arrival time corresponds to a time (t(i)) in the temporal sequence at which a predetermined contrast enhancement due to the contrast medium and/or marked blood components filling first occurs, determining a data set of temporally inverted bolus arrival times $t_{BAT}^{in}$ with respect to the contrast medium and/or marked blood components filling for each pixel or voxel of the recorded vascular system, the data set being a temporally inverted sequence of frames with respect to the contrast medium and/or marked blood components filling, and visualizing at least a part of the time-resolved angiographic image data set of the vascular system in the temporally inverted sequence with respect to the contrast medium and/or marked blood components filling.

2. The method as claimed in claim 1, wherein the predetermined contrast enhancement due to the contrast medium filling is at least 10% of a maximum contrast.

3. The method as claimed in claim 1, wherein the time-resolved angiographic image data set of the vascular system is formed by a four-dimensional subtraction angiography data set that has a temporal sequence of volume frames of the vascular system corresponding to the contrast medium and/or marked blood components filling process.

4. The method as claimed in claim 1, wherein the time-resolved angiographic image data set of the vascular system is formed by a series of two-dimensional subtraction angiography images.

5. The method as claimed in claim 1, wherein the time-resolved angiographic image data set of the vascular system is formed by a four-dimensional computed tomography data set or a magnetic resonance data set.

6. The method as claimed in claim 1, wherein the time-resolved angiographic image data set of the vascular system in the temporally inverted sequence with respect to the contrast medium and/or marked blood components filling is displayed or played back on a display as a scene.

7. The method as claimed in claim 1, wherein the time-resolved angiographic image data set of the vascular system is displayed or played back as a scene on a display in the temporal sequence corresponding to the process with respect to the contrast medium and/or marked blood components filling and the temporally inverted sequence in alternation.

8. The method as claimed in claim 1, wherein visualizing includes a color gradient.

9. The method as claimed in claim 1, wherein at least one pretrained machine learning algorithm determines the bolus arrival times and/or the inverted bolus arrival times.

10. The method as claimed in claim 1 wherein determining the data set of the temporally inverted bolus arrival times comprises determining using a formula $t_{BAT}^{in}=t(N)-t_{BAT}$.

11. An apparatus comprising:

an image processor configured to provide a time-resolved angiographic image data set of a vascular system, the time-resolved angiographic image data set having a temporal sequence of frames of the vascular system at N times (t(1), . . . , t(N)) corresponding to a contrast medium and/or marked blood components filling process, a computer configured to determine a data set from bolus arrival times $t_{BAT}$ for each pixel or voxel of the frames of the recorded vascular system, wherein the bolus arrival time corresponds to a time (t(i)) in the temporal sequence at which a predetermined contrast enhancement due to the contrast medium and/or marked blood components filling first occurs, and configured to determine a data set of temporally inverted bolus arrival times $t_{BAT}^{in}$ with respect to the contrast medium and/or marked blood components filling for each pixel or voxel of the recorded vascular system, the data set being a temporally inverted sequence of frames with respect to the contrast medium and/or marked blood components filling, a memory configured to store the data sets, and a display configured to display at least a part of the time-resolved angiographic image data set of the vascular system in the temporally inverted sequence with respect to the contrast medium and/or marked blood components filling.

12. The apparatus as claimed in claim 11 further comprising a medical imager configured to record image data sets.

13. The apparatus as claimed in claim 12, wherein the medical imager comprises a C-arm X-ray device embodied for rotation angiography.

14. The apparatus as claimed in claim 11, wherein the computer is configured to determine the data set of the temporally inverted bolus arrival times with a formula $t_{BAT}^{in} = t(N) - t_{BAT}$.

* * * * *